United States Patent [19]

Nagai et al.

[11] Patent Number: 4,824,778

[45] Date of Patent: Apr. 25, 1989

[54] IMMUNOASSAY FOR MEASURING THE CONCENTRATION OF ANTIGEN IN A SAMPLE

[75] Inventors: Keiichi Nagai, Tokyo; Daizo Tokinaga, Hachioji; Kazumichi Imai, Kodaira; Kenji Yasuda, Tokyo; Satoshi Takahashi, Kokubunji; Teruaki Kobayashi, Hachioji, all of Japan

[73] Assignee: Hitachi, Ltd., Tokyo, Japan

[21] Appl. No.: 867,554

[22] Filed: May 28, 1986

[30] Foreign Application Priority Data

May 29, 1985 [JP] Japan .................. 60-114084

[51] Int. Cl.$^4$ ........................... G01N 33/53
[52] U.S. Cl. .................... 435/7; 204/182.8; 204/299 R; 436/515; 436/516
[58] Field of Search ............ 436/516; 435/7; 204/182.8, 299 R

[56] References Cited

U.S. PATENT DOCUMENTS 4,198,389   4/1980   Wadsworth .............. 436/516
4,288,425   9/1981   Lee et al. ............... 436/516
4,452,901   6/1984   Gordon et al. .......... 436/516
4,628,035  12/1986   Tokinaga et al. ........ 436/516

Primary Examiner—Sam Rosen
Attorney, Agent, or Firm—Antonelli, Terry & Wands

[57] ABSTRACT

An immunoassay comprising
immobilizing antibody in a matrix for electrophoresis;
immobilizing antigen in a measurement sample by subjecting the same to antigen antibody reaction with the above-mentioned immobilized antibody by a procedure of moving the antigen by electrophoresis;
either moving labeled antibody to the above-mentioned immobilized antigen by electrophoresis to react the same with the immobilized antigen, or moving labeled antigen to the unreacted portion of the above-mentioned immobilized antibody by electrophoresis to react the same with the unreacted portion; and
measuring the concentration of antigen in the sample, characterized by
using as a label for the labeled antibody or the labeled antigen an enzyme capable of coverting a substrate into a fluorescent substance,
moving the substrate convertible into a fluorescent substance by said enzyme by electrophoresis,
reacting the substrate with the label enzyme to convert the same into a fluorescent substance, and
measuring the concentration of the fluorescent substance in the electrolyte solution.

3 Claims, 1 Drawing Sheet

IMMUNOASSAY FOR MEASURING THE CONCENTRATION OF ANTIGEN IN A SAMPLE

BACKGROUND OF THE INVENTION

This invention relates to a method for measuring the concentration of antigen using immunoassay, particularly to a method suitable for measuring it with high sensitivity by measuring fluorescence.

Since there was reported a method for determining a slight amount of insulin by using a specific antibody labeled with a radioisotope, this determination method called radioimmunoassay has come to be utilized for quantitating various biological substances and drugs. However, it is disadvantageous in that it uses radioisotopes, so that special care must be taken in handling them. Therefore, various kinds of immunoassays utilizing nonradioactive labels such as enzymes, substrates, fluorescent substances, chemiluminescent substances and the like are investigated, and among these, methods using an enzyme or a fluorescent substance as a label have reached the practical use stage. In particular, a fluorometric method using a fluorescent label permit determination in a short time. However, this method is also difficult to automate because its whole process requires labor and time. In order to simplify the whole process, there has been proposed a method for measuring the concentration of antigen in a sample which comprises immobilizing antibody in a membranous matrix, applying a gradient of electric potential perpendicular to the surface of the membrane, thereby moving the antigen in the measurement sample in this direction by electrophoresis, subjecting the antigen to antigen antibody reaction with the above-mentioned immobilized antibody to immobilize the same, immobilizing a label in the membranous matrix either by moving labeled antibody to the antigen immobilized by the above-mentioned procedure by electrophoresis to label the immobilized antigen, or by moving labeled antigen to the unreacted portion of the antibody immobilized in the membranous matrix by electrophoresis to label the unreacted immobilized antibody, and then measuring the concentration of the immobilized label to calculate that of the immobilized antigen. (Japanese Patent Publication Kokai (Laid-Open) No. 57257/85).

According to this method, the matrix for electrophoresis in which antigen or antibody is immobilized is in contact, on one side, with the electrolytic solution on the cathode side, and on the other side, with the electrolytic solution on the anode side, so that the time required for antigen antibody reaction which has been 3 hours to 1 day in conventional immunoassay methods can be reduced to 1 hour or less. Further, the process of conventional immunoassay can be simplified. In detail, since the unreacted substances and surplus labeled antibody penetrate the reaction membrane and move to the lower electrolytic solution, the procedure of washing with water which is necessary in immunoassay based on conventional solid-phase reaction becomes unnecessary.

However, although the above-mentioned immunoassay using electrophoresis permits simplification of the whole process and is suitable for automation of apparatus, it is disadvantageous in that when the concentration of antigen in a sample is measured by fluorometry by using antibody or antigen labeled with a fluorescent substance, scattered light and interfering fluorescence are serious.

SUMMARY OF THE INVENTION

An object of this invention is to provide a highly sensitive means of fluorescence measurement in an immunoassay comprising carrying out antigen antibody reaction by electrophoresis in a membranous matrix in which antibody is immobilized.

Another object of this invention is to provide an immunoassay comprising
  immobilizing antibody in substantially the whole portion of a matrix for electrophoresis,
  immobilizing antigen in a measurement sample by subjecting the same to antigen antibody reaction with the above-mentioned immobilized antibody by a procedure of moving the antigen by electrophoresis,
  either moving labeled antibody to the abovementioned immobilized antigen by electrophoresis to react the same with the immobilized antigen, or moving labelled antigen to the unreacted portion of the above-mentioned immobilized antibody by electrophoresis to react the same with the unreacted portion, and
  thereby measuring the concentration of antigen in the sample, which is characterized in that the concentration of antigen in the sample is measured by
  using as a label an enzyme capable of converting a substrate into a fluorescent substance,
  moving the substrate convertible into a fluorescent substance by said enzyme by electrophoresis,
  reacting the substrate with the label enzyme to convert the same into a fluorescent substance,
  moving said fluorescent substance from the matrix for electrophoresis to electrolytic solution, and then
  measuring the concentration of the fluorescent substance, which is in proportion to that of the label enzyme, that is, the concentration of antigen in the sample; that no procedure of washing with water is needed; and that scattered light and interfering fluorescence hardly occur.

DETAILED DESCRIPTION OF PREFERRED EMBODIMENTS

Figure 1:
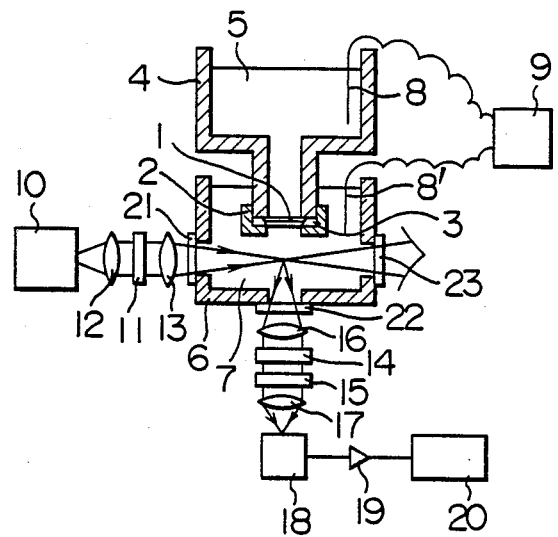
FIG. 1 is a constitution diagram of one example of this invention.

In general, in the case of determination of fluorescence emitted by a fluorescent substance in a membrane, it is difficult to measure the amount of fluorescence with high sensitivity because scattered light due to the membrane or background fluorescence from constitutive substances of the membrane is serious. On the other hand, in the case of determination of fluorescence emitted by a fluorescent substance in an aqueous solution, highly sensitive fluorescence measurement can be realized because the above-mentioned interfering luminescence is slight.

Accordingly, in this invention, instead of directly measuring the amount of a label fluorescent substance in a membrane, the amount of fluorescence of a fluorescent substance is measured in an electrolytic solution by using as a label an enzyme capable of converting a substrate into a fluorescent substance, reacting the aforesaid enzyme immobilized by antigen antibody reaction in a membrane, i.e., a matrix for electrophoresis, with a substrate moved into the aforesaid membrane by electrophoresis, thereby converting the substrate into a fluorescent substance, and moving the fluorescent substance into the electrolytic solution. For the reason described above, the amount of fluorescence of the fluorescent substance in the electrolytic solution can be measured with high sensitivity. Further, according to this invention, a plurality of substrate molecules per molecule of the label enzyme can be converted into a fluorescent substance by allowing a large amount of substrate molecules to penetrate the membrane, so that there can be obtained fluorescent substance molecules more than labeled antibody or antigen molecules immobilized in the membrane. By virtue of also this fact, highly sensitive fluorescence measurement can be realized.

As such an enzyme, there are known several enzymes such as peroxidase, alkaline phosphatase, esterase and the like. Peroxidase converts substrates, 3-p-hydroxyphenylpropionic acid and p-hydroxyphenylacetic acid into fluorescent substances. Alkaline phosphatase converts a substrate, 4-methyl-umbelliferyl phosphate into a fluorescent substance. Esterase converts a substrate, fluorescein diacetate into a fluorescent substance. As a method for immobilizing an enzyme on the antigen or antibody, a well-known glutaraldehyde method or the like is used. This method is described, for example, in Immunochemistry, 6, 43(1969).

For increasing the concentration of the fluorescent substance moved into the electrolytic solution in the above-mentioned process, it is preferable that the amount of the electrolytic solution in an electrolytic solution bath is small. On the other hand, when the amount of the electrolytic solution is too small, there is possibility that the constituents of the electrolytic solution are changed during electrophoresis, so that appropriate electrophoresis is not carried out. Therefore, as a more preferred embodiment of this invention, there is a method which comprises dividing the electrolytic solution bath on the side on which the fluorescent substance comes out, into two sections by a membrane which is permeable to electrolytes in the electrolytic solution but impermeable to the fluorescent substance, and thereby making it possible to concentrate the fluorescent substance in a section having a small capacity without changing the composition of electrolytes in the electrolytic solution. As such a membrane, any one may be used so long as it has the following structure: it is pierced with many pores in the direction of its thickness, and the diameter of its pores is so small that it is permeable to small ions in the electrolyte but impermeable to relative large ions. There are used, for example, porous glass thin plates, porous cellulose acetate films, porous polyhydroxyethyl methacrylate films, etc. The volume of the section having a small capacity in which the fluorescent substance is concentrated is preferably 1 cm$^3$ or less. The preferable volume is calculated from a concentration of about $10^{-13}$ mole/liter or more at which determination of the fluorescent substance is easy.

One example of this invention is explained referring to FIG. 1. The reaction membrane 1 which was a matrix for electrophoresis was a polyacrylamide gel film of about 300 μm in thickness, in which anti-human albumin antibody (rabbit) was immobilized. The reaction film 1 can be prepared in a manner mentioned below. First, 25 μl of 2.5% acrolein aqueous solution was added to 0.5 ml of IgG fraction (containing 2.4 mg/ml of active antibody component) of anti-human albumin antiserum, and the resulting mixture was allowed to stand with ice-cooling for 30 minutes and then sufficiently dialyzed against PBS. To the dialyzed mixture were added 1.5 ml of an acrylamide aqueous solution having a concentration of 0.32 g/ml, 1.5 ml of an N,N'-methylene bisacrylamide aqueous solution having a concentration of 0.016 g/ml, 1.25 ml of an N,N,N',N'-tetramethylethylenediamine aqueous solution having a concentration of 4.6 μl/ml, and 5.75 ml of an ammonium persulfate aqueous solution having a concentration of 1.2 mg/ml. The resulting mixture was sufficiently stirred, then poured into a gel film-forming-vessel made of glass, and allowed to stand to be gelatinized, whereby a film was formed. A circular film having a diameter of 9 mm was cut out of the thus formed film and held by means of a film holder 2 made of acrylic resin. In consideration of the brittleness of the polyacrylamide gel film in which the antibody had been immobilized, a spacer ring 3 made of polyester and having a thickness of 200 μm was inserted around the reaction membrane.

A mixture of a human albumin standard sample and sucrose was poured into an electrolytic solution 5 in an upper electrolytic solution bath 4, after which electrophoresis was carried out for 30 minutes by applying a voltage of 250 V between a platinum electrode 8 in the upper electrolytic solution and a platinum electrode 8' in the lower electrolytic solution bath 6 by means of a direct current electric source 9.

Further, anti-human albumin antiserum (rabbit) labeled with esterase was poured similarly into the electrolytic solution 5 in the upper electrolytic solution bath 4, after which electrophoresis was carried out at an applied voltage of 250 V for 20 minutes in the same manner as described above.

Next, FDA (fluorescein diacetate) which was a substrate for the label enzyme esterase was poured similarly into the electrolytic solution 5 in the upper electrolytic solution bath 4, and then electrophoresis was carried out at an applied voltage of 250 V for 30 minutes.

The intensity of fluorescence of a fluorescent substance, fluorescein released into an electrolytic solution 7 in the lower electrolytic solution bath 6 by the above-mentioned procedure was measured by using a Xe lamp 10 as a light source for excitation. Light having a wavelength of 490 nm was selected by means of an interference filter and passed through an optical window 21 by use of lenses 12 and 13 to excite the fluorescent substance in the lower electrolytic solution 7. The fluorescence was passed through an optical window 22, lenses 16 and 17, an interference filter 15 and a cut-off filter 14 in a direction perpendicular to the excitation light, and light having a wavelength near 510 nm was selectively detected by means of a photomultiplier tube 18. The excitation light transmitted by the lower electrolytic solution 7 was conducted to the outside through an optical window 23. By use of the above-mentioned optical system, fluorescence measurement hardly influenced by scattered light could be carried out. The output of the photomultiplier tube 18 was recorded by means of a recorder 20. An apparatus having the structure shown in FIG. 1 could realize determination of the human albumin standard sample with good quantitativeness and high sensitivity.

Figure 2:
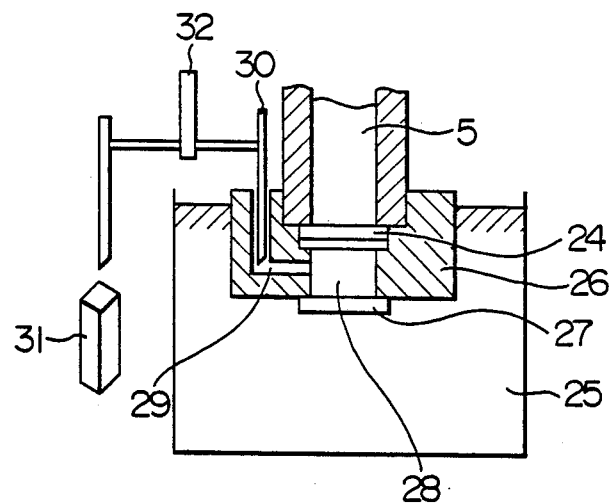
FIG. 2 is a partial constitution diagram of one example of this invention.

Another example of this invention is explained referring to FIG. 2. A method for preparing a reaction membrane 24, the structure of electrolytic solution baths, and antigen antibody reaction and enzymic reaction by electrophoresis were the same as in the example shown in FIG. 1. In this example, an electrolytic solution bath 28 having a small capacity was produced by disposing a porous glass plate 27 attached to a plate holder 26 made of acrylic resin, between the reaction membrane 24 and a lower electrolytic solution 25. The aforesaid porous glass was produced by reacting tetramethoxysilane with methanol in an aqueous solvent by a sol gel method, and was quartz glass which was permeable to electrolytes in the electrolytic solution but impermeable to the fluorescent substance. Therefore, a substrate converted into a fluorescent substance by the enzyme immobilized in the reaction membrane 24 was concentrated in the electrolytic solution bath 28. In the present example, an electrolytic solution containing the fluorescent substance concentrated by the above-mentioned procedure was passed through a guide hole 29 and introduced into a fluorescence cuvette 31 by using a pipette 30. The pipette was held by means of a rotary up-and-down device 32. The fluorescent substance in the fluorescence cuvette 31 was subjected to fluorescence measurement by using the same optical system as explained in FIG. 1. The present example could realize more highly sensitive measurement of the concentration of antigen in a sample.

According to this invention, in an immunoassay suitable for automation comprising measuring the concentration of antigen in a sample by carrying out antigen antibody reaction in a membrane which is a matrix for electrophoresis, fluorescence measurement in an aqueous solution can be made possible by converting a large amount of substrate molecules into a fluorescent substance by use of a label enzyme immobilized in the membrane whose concentration is proportional to the concentration of the antigen, and moreover a means of concentrating the fluorescent substance in a section having a small capacity can be provided. Therefore, highly sensitive measurement of the concentration of antigen becomes possible.

What is claimed is:

1. An immunoassay comprising:
immobilizing antibody in substantially the whole portion of a matrix for electrophoresis;
immobilizing antigen in a measurement sample by subjecting the same to antigen antibody reaction with the above-mentioned immobilized antibody by a procedure of moving the antigen by electrophoresis;
either moving labeled antibody to the above-mentioned immobilized antigen by electrophoresis to react the same with the immobilized antigen, or moving labeled antigen to the unreacted portion of the above-mentioned antibody by electrophoresis to react the same with the unreacted portion;
measuring the concentration of antigen in the sample, characterized by using as a label for the labeled antibody or the labeled antigen an enzyme capable of converting a substrate into a fluorescent substance,
moving the substrate convertible into a fluorescent substance by said enzyme by electrophoresis,
reacting the substrate with the label enzyme to convert the same into a fluorescent substance,
moving said fluorescent substance from the matrix for electrophoresis to electrolytic solution, and then
measuring the concentration of the formed fluorescent substance in the electrolyte solution.

2. An immunoassay according to claim 1, wherein an electrolytic solution bath to which the fluorescent substance is moved is divided into two sections by a membrane which is permeable to electrolytes but impermeable to the fluorescent substance.

3. An immunoassay method comprising immobilizing an antibody in substantially the whole portion of a matrix for electrophoresis;
moving an antigen in a measurement sample by electrophoresis to the immobilized antibody to immobilize the antigen by an antigen reaction;
moving a labeled antibody to the immobilized antigen by electrophoresis to react with the immobilized antigen, or moving a labeled antigen to the immobilized antibody which has not reacted with the antigen by electrophoresis to react with the immobilized antibody;
measuring the concentration of antigen in the sample, characterized by,
using as a label for the labeled antibody or the labeled antigen an enzyme capable of converting a substrate into a fluorescent substance,
moving the substrate past said label enzyme by electrophoresis to convert the substrate into a fluorescent substance,
moving the fluorescent substance away from the matrix to an electrolytic solution, and
measuring the concentration of the fluorescent substance in the electrolyte solution.

* * * * *